United States Patent
Rivlin et al.

(10) Patent No.: US 12,217,449 B2
(45) Date of Patent: Feb. 4, 2025

(54) SYSTEMS AND METHODS FOR VIDEO-BASED POSITIONING AND NAVIGATION IN GASTROENTEROLOGICAL PROCEDURES

(71) Applicant: Verily Life Sciences LLC, South San Francisco, CA (US)

(72) Inventors: Ehud Benyamin Rivlin, Tel Aviv (IL); Yossi Matias, Tel Aviv (IL)

(73) Assignee: Verily Life Sciences LLC, Dallas, TX (US)

( * ) Notice: Subject to any disclaimer, the term of this patent is extended or adjusted under 35 U.S.C. 154(b) by 392 days.

(21) Appl. No.: 17/614,227

(22) PCT Filed: May 22, 2020

(86) PCT No.: PCT/US2020/034245
§ 371 (c)(1),
(2) Date: Nov. 24, 2021

(87) PCT Pub. No.: WO2020/242949
PCT Pub. Date: Dec. 3, 2020

(65) Prior Publication Data
US 2022/0254017 A1  Aug. 11, 2022

Related U.S. Application Data

(60) Provisional application No. 62/853,535, filed on May 28, 2019.

(51) Int. Cl.
*A61B 34/10* (2016.01)
*A61B 1/00* (2006.01)
(Continued)

(52) U.S. Cl.
CPC .......... *G06T 7/70* (2017.01); *A61B 1/000094* (2022.02); *A61B 1/000096* (2022.02);
(Continued)

(58) Field of Classification Search
CPC ..................................................... G16H 50/20
See application file for complete search history.

(56) References Cited

U.S. PATENT DOCUMENTS

| 8,020,993 B1* | 9/2011 | Fram .................. G06F 3/013 |
| | | 351/200 |
| 2016/0113632 A1* | 4/2016 | Ribes .................. A61B 8/469 |
| | | 600/440 |

(Continued)

OTHER PUBLICATIONS

International Search Report and Written Opinion mailed Sep. 22, 2020, issued in corresponding International Application No. PCT/US2020/034245, filed May 22, 2020, 9 pages.

(Continued)

*Primary Examiner* — Di Xiao
(74) *Attorney, Agent, or Firm* — Christensen O'Connor Johnson Kindness PLLC

(57) ABSTRACT

The present disclosure provides systems and methods for improving detection and location determination accuracy of abnormalities during a gastroenterological procedure. One example method includes obtaining a video data stream generated by an endoscopic device during a gastroenterological procedure for a patient. The method includes generating a three-dimensional model of at least a portion of an anatomical structure viewed by the endoscopic device based at least in part on the video data stream. The method includes obtaining location data associated with one or more detected abnormalities based on localization data generated from the video data stream of the endoscopic device. The method includes generating a visual presentation of the three-dimensional model and the location data associated with the one or more detected abnormalities; and providing the visual presentation of the three-dimensional model and the location data associated with the detected abnormality for use in diagnosis of the patient.

17 Claims, 8 Drawing Sheets

(51) Int. Cl.
*A61B 5/00* (2006.01)
*A61B 34/20* (2016.01)
*G06T 7/00* (2017.01)
*G06T 7/70* (2017.01)
*G06T 17/00* (2006.01)

(52) U.S. Cl.
CPC .......... *A61B 5/4255* (2013.01); *A61B 5/7267* (2013.01); *A61B 34/10* (2016.02); *A61B 34/20* (2016.02); *G06T 7/0012* (2013.01); *G06T 17/00* (2013.01); *A61B 2034/105* (2016.02); *G06T 2207/10016* (2013.01); *G06T 2207/10068* (2013.01); *G06T 2207/30032* (2013.01); *G06T 2207/30092* (2013.01); *G06T 2207/30096* (2013.01)

(56) References Cited

U.S. PATENT DOCUMENTS

| | | | | |
|---|---|---|---|---|
| 2017/0221271 | A1* | 8/2017 | Mullins | G06F 3/1454 |
| 2017/0372193 | A1* | 12/2017 | Mailhe | G06N 3/02 |
| 2018/0103938 | A1* | 4/2018 | Stoianovici | A61B 10/0241 |
| 2018/0247107 | A1* | 8/2018 | Murthy | G06V 20/698 |
| 2019/0151025 | A1* | 5/2019 | Brannan | A61B 34/25 |
| 2021/0137634 | A1* | 5/2021 | Lang | A61B 5/113 |

OTHER PUBLICATIONS

Pahlavan, K., et al., "A Novel Cyber Physical System for 3-D Imaging of the Small Intestine In Vivo", IEEE Access, Dec. 11, 2015, pp. 2730-2742.

Dixit, P. K., et al., "Polyp Shape Estimation from Endoscopy Video Using EKF Monocular SLAM with SFS Model Prior", IEEE Wispnet Conference, Mar. 22, 2017, pp. 52-57.

Chen, L., et al., "SLAM-based Dense Surface Reconstruction in Monocular Minimally Invasive Surgery and its Application to Augmented Reality", Feb. 8, 2018, pp. 135-146.

Armin, M. A., et al., "Automated visibility map of the internal colon surface from colonoscopy video", Int J CARS, Aug. 4, 2016, pp. 1599-1610.

Junseok, P., et al., "Recent Development of Computer Vision Technology to Improve Capsule Endoscopy", Clinical Endoscopy, Feb. 21, 2019, pp. 328-333.

Office Action mailed Dec. 9, 2024, in corresponding European application No. 20732051.6, filed May 22, 2020, 7 pages.

* cited by examiner

SYSTEMS AND METHODS FOR VIDEO-BASED POSITIONING AND NAVIGATION IN GASTROENTEROLOGICAL PROCEDURES

CROSS REFERENCE TO RELATED APPLICATIONS

This application is a National Stage of International Application Number PCT/US2020/034245, filed May 22, 2020, which claims priority to and the benefit of U.S. Provisional Patent Application No. 62/853,535 filed May 28, 2019. U.S. Provisional Patent Application No. 62/853,535 and PCT Application Number PCT/US2020/034245 are hereby incorporated by reference herein in their entirety for all purposes.

FIELD

The present disclosure relates generally to computing systems and methods that enable improved performance of gastroenterological procedures. More particularly, the present disclosure relates to using machine-learned models and/or video-based positioning and navigation to improve detection and/or localization of abnormalities during gastroenterological procedures.

BACKGROUND

In many medical procedures that use a camera for examination there is a need to position and navigate the device in use, such as in gastroenterological procedures like colonoscopies and/or when analyzing data from wireless capsule endoscopy.

In particular, a colonoscopy or other gastroenterological procedure can be performed to search for and identify abnormalities (e.g., polyps, lesions, tumors, etc.) within a patient's colon or other portions of the patient's gastrointestinal tract. Typically, a gastroenterological procedure is performed through insertion of an endoscopic device that includes a camera (e.g., a wired camera or wireless camera) into the patient's digestive tract. The device then captures imagery while it moves through the patient's digestive tract (e.g., due to manual guidance/manipulation of the device or due to natural action of the patient's body). A physician may review the imagery (e.g., during the procedure and/or after performance of the procedure) to attempt to visually identify any abnormalities, such as abnormalities that may be associated with or symptoms of colorectal cancer (CRC).

CRC and other gastroenterological diseases are a major healthcare issue that impacts millions of persons globally. However, current attempts to diagnose these diseases (e.g., via performance of gastroenterological procedures such as colonoscopies) suffer from a number of drawbacks. As examples, there is a lack of patient insight into and objective performance measures of gastroenterological procedures. Thus, there is a need for systems which enable improved feedback regarding procedures.

Furthermore, visual identification of abnormalities within a patient's colon or other portions of the patient's gastrointestinal tract is a highly challenging task. For example, research has shown a significant miss rate (e.g., approximately twenty-five percent) for different types of polyps when tested in back to back colonoscopies. Thus, there is a need for systems which assist physicians in the detection of abnormalities.

Accurate localization of any abnormalities detected during a gastroenterological procedure is also very important in order to determine adequate surgical treatment. For example, even assuming an abnormality is correctly detected, the accurate localization of such abnormality within the gastrointestinal tract is highly valuable to reduce the challenge of and complications associated with subsequent surgical treatment (e.g., removal) of the abnormality. Accurate localization may be even more relevant under certain circumstances, such as in cases of endoscopically resected malignant polyps which may require further surgery, small or flat tumors that are difficult for surgical localization, and/or the like. Thus, there is a clear need to document precise locations of abnormalities (and associated biopsies and samples) for further follow up procedures, such as future endoscopic examination and/or surgery.

SUMMARY

Aspects and advantages of embodiments of the present disclosure will be set forth in part in the following description, or can be learned from the description, or can be learned through practice of the embodiments.

One example aspect of the present disclosure is directed to a computer-implemented method for using video-based positioning and navigation for detection and location determination of abnormalities during a gastroenterological procedure. The method includes obtaining, by one or more computing devices, a video data stream generated by an endoscopic device during a gastroenterological procedure for a patient. The method includes generating, by the one or more computing devices, a three-dimensional model of at least a portion of an anatomical structure viewed by the endoscopic device based at least in part on the video data stream. The method includes obtaining, by the one or more computing devices, location data associated with one or more detected abnormalities based on localization data generated from the video data stream of the endoscopic device. The method includes generating, by the one or more computing devices, a visual presentation of the three-dimensional model and the location data associated with the one or more detected abnormalities. The method includes providing, by the one or more computing devices, the visual presentation of the three-dimensional model and the location data associated with the detected abnormality for use in diagnosis of the patient.

Another example aspect of the present disclosure is directed to a computing system. The computing system includes one or more processors; and one or more non-transitory computer-readable media that store instructions. The instructions, when executed by the one or more processors, cause the computing system to perform operations. The operations include obtaining a video data stream generated by an endoscopic device during a gastroenterological procedure for a patient. The operations include generating a three-dimensional model of at least a portion of an anatomical structure viewed by the endoscopic device based at least in part on the video data stream. The operations include obtaining location data associated with one or more detected abnormalities based on localization data generated from the video data stream of the endoscopic device. The operations include generating a visual presentation of the three-dimensional model which visualizes the location data associated with the one or more detected abnormalities. The operations include providing the visual presentation of the three-dimensional model and the location data associated with the one or more detected abnormalities for use in diagnosis of the patient.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1:
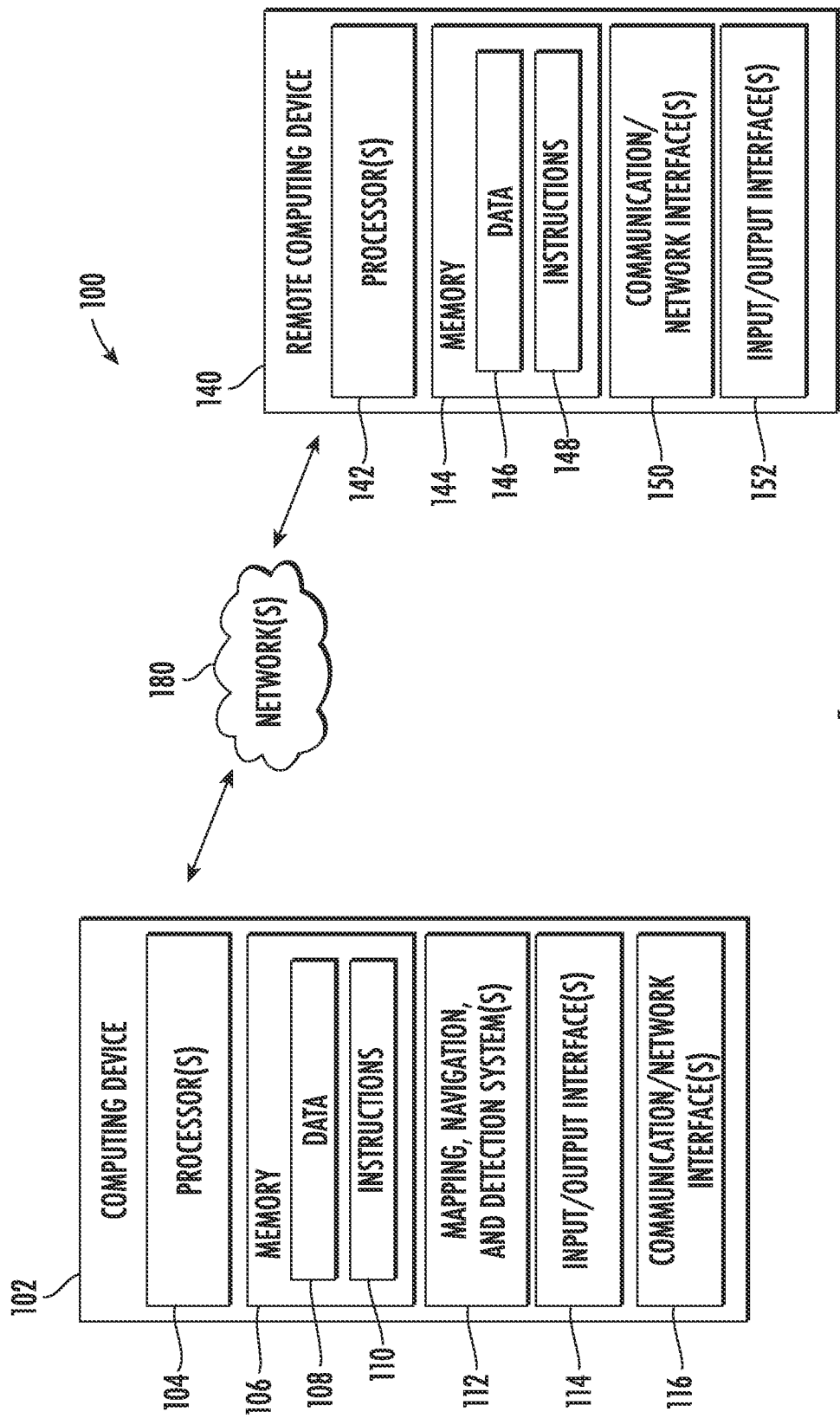
FIG. 1 depicts a block diagram of computing system according to example embodiments of the present disclosure.

Reference numerals that are repeated across plural figures are intended to identify the same features in various implementations.

DETAILED DESCRIPTION

Overview

Example aspects of the present disclosure are directed to systems and methods for improving detection and localization accuracy of abnormal sites (e.g., adenoma, polyp, lesion, tumor, etc.) during a gastroenterological procedure using video-based positioning and navigation. In particular, the systems and methods of the present disclosure can provide for improvements in detecting abnormalities (e.g., polyps, lesions, tumors, etc.) and determining more precise locations of abnormalities (e.g., polyps, lesions, tumors, etc.) based on video signal data from an endoscopic device (e.g., standard endoscope, wireless capsule endoscopy, etc.) during gastroenterological procedures (e.g., colonoscopies, etc.). For example, according to one aspect of the present disclosure, the systems and methods of the present disclosure can analyze the video signal data to generate abnormality detection and/or re-detection probabilities, for example, through use of trained machine-learning models (e.g., trained using labeled image data, etc.). According to another aspect of the present disclosure, real time processing of video signal input (e.g., from an endoscopic device) can enable more precise localization, positioning, and navigation of an endoscopic device during a patient procedure, thereby improving polyp detection rates and providing for the generation of visual presentations of procedure data, such as presentations of a three-dimensional model of the colon or other internal organ, along with positions of detected abnormalities (e.g., polyps, tumors, etc.). According to other aspects of the present disclosure, the systems and methods can provide for generation of a visibility map based on the localization, positioning, and navigation of the endoscope, for example to allow for determination of unviewed areas. According to yet other aspects of the present disclosure, the systems and methods can provide for improvements in the safety of gastroenterological procedures, for example, allowing for the identification and mitigation of looping of the endoscope shaft during a procedure, facilitating reductions in patient discomfort level/pain level during a procedure, and/or the like. Thus, the systems and methods of the present disclosure can provide for improvements in the performance of gastroenterological procedures as well as improvements in the detection rate and reliability of detection of an overall procedure.

More particularly, aspects of the present disclosure are directed to computing systems which analyze video signal data captured by a camera of an endoscopic device to both detect abnormalities shown in the imagery and localize the camera and abnormalities relative to the various structure(s) of the gastroenterological tract. In particular, the computing systems described herein can perform one or more simultaneous localization and mapping (SLAM) techniques to generate a three-dimensional model of a colon or other internal organ (e.g., stomach or small intestine) or anatomical structure. This process can also simultaneously determine a position of the camera (e.g., endoscope, WCE, etc.) in the colon at all times during a gastroenterological procedure.

In particular, SLAM provides for constructing and/or updating a model of an unknown environment (e.g., a particular patient's colon) while simultaneously keeping track of the camera position within the environment. In some implementations, special treatment can be given to the correspondence process of images as, for example in the case of a colonoscopy, the camera and the light source are correlated, and consequently corresponding points will not necessarily have the same appearance and as such finding corresponding points can be challenging. Thus, using SLAM techniques, the computing system can generate and/or update a three-dimensional model of portions of the anatomical structure (e.g., colon, etc.) of the patient viewed by the endoscopic device along with position data associated with polyps, tumors, and/or other abnormalities detected during the gastroenterological procedure. Additionally, in some implementations, the computing system can provide for using additional process to assist in reconstruction of the three-dimensional structure, such as for example, determining surface shape from shading based on knowledge of the camera and light source (e.g., endoscopic device, etc.) positioning within the anatomical structure (e.g., colon, etc.).

In addition to performing SLAM to build a model of the anatomical structure and localize the device relative to the anatomical structure, in some implementations, the computing systems described herein can also analyze the captured imagery to automatically visually detect abnormalities during or after the procedure. In particular, some implementations of the present disclosure may include and use one or more machine-learned models that have been trained for generating abnormality (e.g., polyp, lesion, tumor, etc.) detection and/or re-detection probabilities during a gastroenterological procedure based on video data captured by the endoscopic device. For example, one or more machine-learned models can be trained to determine a probability for an abnormality detection based on a corpus of labeled image data (e.g., labeled image data from prior examinations where abnormalities have been detected, etc.). In some implementations, the systems and methods can provide for detection of abnormalities that may be on-screen for only one or two frames (e.g., which may be difficult for a human operator to spot), thus providing an improvement in abnormality detection relative to human analysis.

According to an aspect of the present disclosure, the computing system can generate one or more visual representations of the three-dimensional model, the position of the endoscopic device, and/or position(s) of the detected polyp(s) and/or other abnormalities. The visual representations can be used in diagnosis, treatment, performance review, and/or the like (e.g., optical biopsy, surgical determination, future endoscopic procedure, etc.). In particular, in some implementations, the generation and presentation of such visual representations can be performed in real-time during the procedure to assist in performance of the procedure, including providing real-time navigation assistance for the device operator. Alternatively or additionally, various visual representations can be generated at a conclusion or following the procedure in the form of a summary visualization, report, and/or the like.

As one example visual representation, the computing system can generate and present a heads up display in which abnormality detections generated by the machine-learned model are overlaid (e.g., in real-time) upon imagery captured by the endoscopic device. For example, any detections included in the currently displayed imagery can be indicated through the use of a bounding box or other visual indicator to indicate the location of the detected abnormality within the image. In some implementations, in addition to detection of the abnormalities, the computing system (e.g., machine-learned models used thereby) can also predict the pathological makeup of the abnormality. In such implementations, the pathological prediction can also be provided in the heads up display (e.g., in the form of a classification with confidence value). Likewise, any detected landmarks (e.g., specific anatomical structures) can be identified with a visual indicator in the heads up display as well.

Furthermore, in some implementations, the heads up display can include visual indicators (e.g., small arrows) that indicate when a detected abnormality is near, but not currently depicted within the current field of view of the endoscopic device. Thus, by localizing both the abnormality and the device (e.g., relative to each other and/or the greater anatomical structure), the systems and methods of the present disclosure can enable the heads up display to indicate when an abnormality is just "off-screen" or otherwise only slightly out of the current field of view of the device camera.

As another example, the computing system can generate a visual presentation of the three-dimensional model and current position/viewpoint of the endoscopic device within the three-dimensional model. For example, an interactive two-dimensional rendering of the three-dimensional model can be provided. The interactive rendering can be movable, zoomable, rotatable, and/or the like. The respective location(s) of any detected abnormalities and/or landmarks can also be shown relative on the model. Thus, such a visual representation can enable the device operator (e.g., physician) to easily and intuitively understand the current position of the endoscopic device relative to the anatomical structure and/or previously detected abnormalities. Such understanding can improve the operator's ability to thoroughly and correctly examine the anatomical structure.

As yet another example visual presentation, the computing system can generate a visibility map associated with the anatomical structure (e.g., colon) being examined. By reconstructing the local three-dimensional structure, a visibility map can be generated and presented to the operator (e.g., gastroenterologist). The visibility map can provide a visual overlay of unviewed areas and/or sub-optimally exposed/viewed areas on the local three-dimensional structure, thus drawing attention (e.g., in real-time) to areas in need of further examination for abnormalities, thereby improving the detection rate of the overall procedure. For example, in some implementations, the systems and methods can provide for real-time directional alerts (e.g., within the heads up display) indicating where the camera is not oriented properly, thereby indicating areas that may not have been fully examined.

In some implementations, the output (e.g., including the visual representations) can further include any operator (e.g., physician) generated notes made during the examination and/or the like. For example, specific notes can be associated with each abnormality. This output can then be used in diagnosis and/or treatment of the patient, for example, with regard to biopsy, surgical procedures, future endoscopy procedures, and/or the like.

Additionally, in some implementations, the computing system can obtain data (e.g., heart rate, etc.) that may be indicative of patient pain level and/or discomfort level and generate indications of an estimated patient pain level and/or discomfort level in one or more visual representations (e.g., heads up display, procedure performance report, etc.). For example, providing indications of a patient pain level and/or discomfort level can facilitate adjustments to the operation of the endoscopic device and/or the like during a gastroenterological procedure to reduce and/or avoid pain and/or discomfort levels for the patient, and additionally provide for improved patient safety during a gastroenterological procedure.

Additional aspects of the present disclosure are directed to improvements to the SLAM or other localization process which leverage knowledge of the structure of the anatomical location being analyzed. As one example, in some implementations, it is assumed that the object under examination (e.g., colon, etc.) is not a rigid structure, as it can undergo fluctuations during the procedure. Thus, as the process continues on more video frames, the error in the three-dimensional structure can naturally increase. To resolve this issue, more recent images can be given more weight or confidence during the localization process and/or the three-dimensional structure can be allowed to float or otherwise morph over time. Likewise, the same region can often be scanned twice, first in the inward direction and second in the outward direction, and the two scans can be combined to generate a more accurate three-dimensional model.

In some implementations, the systems and methods can exploit the fact that the approximate structure of the structure under examination (e.g., colon, etc.) is known, for example, by using standard atlases of colons in generating the three-dimensional model. Further, in some implementations, landmark detection can further allow for improved positioning, navigation, and detection during a gastroenterological procedure. For example, in some cases, such as in the little and large intestines, the position where the intestine twists can be quite easily detected and therefore the position of the polyp can be defined as or associated with the part of the intestine between the twists and the distance from the last twist. Additionally, the detection of important landmarks can provide for determination of inspection adequacy (e.g., appropriate inspection velocity etc.) as well as provide for later performance review of the procedure.

According to other aspects of the present disclosure, in some implementations, both global and local SLAM can be performed. The local and global SLAM can be provided for different purposes. For example, while the global SLAM can be performed to determine the position of the polyps and the pose of the camera as accurate as possible, the local SLAM can be performed to recover the local three-dimensional shape accurately in order to merge the detections and estimate the orientation of the polyp as accurately as possible, for example, to help determine the prior probability that the detector detects the polyp. This can be used to combine the detection results into a robust accurate detection probability.

For example, in some implementations, in addition to the global SLAM used in global localization for documenting abnormality (e.g., polyp, etc.) locations, the systems and methods can use the local structure to improve abnormality (e.g., polyp, etc.) detection. In such cases, the problem of accumulated errors may be less severe as the accurate position of the camera may not be needed. For example, in some implementations, polyp detection can be performed on a single image, and in order to perform such detection in video data, the systems and methods have to be able to differentiate between a detection of a new polyp and a re-detection of a previously detected polyp. To do so, the detection component can use the three-dimensional reconstruction of a local region providing for more reliable re-detection.

Thus, as the detection is being performed on corresponding regions depicted by several images, one challenge is to combine the results into a single detection decision. On the one hand, the detections performed on frames in the video taken at close proximity may be highly correlated and have to be dealt with. In addition, irrespective of the type of detector used, performance can depend on the imaging conditions such lighting, scale, and viewpoint with respect to the polyp. In some implementations, the systems and methods use the images and more importantly the local three-dimensional reconstruction to estimate the prior probability that the detection is correct. This information can then be used in combining the single image detection results. In some implementations, the results can also be used to retrain the detectors to improve their performance on hard to detect cases.

In some implementations, the colon or other anatomical structure can be divided into a number of distinct local regions and each local region can be separately constructed through separate SLAM solutions. The respective models of the multiple different local regions can then be combined based on a generic colon model. For example, the models can be stitched together with the relative stitching positions being based on correspondences between the regions in combination with overall structure guidance from the generic model.

In some implementations, external information from the motion of the endoscope can be used as additional input to the local three-dimensional reconstruction. For example, the accurate estimation on the overall translation (e.g., wire motion) can provide additional information that may be used in similar way to odometery (e.g., the use of data from motion sensors to estimate change in position over time).

According to another aspect of the present disclosure, in some implementations, the systems and methods of the present disclosure can provide for decision support during a gastroenterological procedure. For example, in some implementations, the use of machine-learned detector models can provide for histological outcome or pathological makeup predictions based on optical features of a detected abnormality. As such, the systems and methods can provide an ability to resect and discard an abnormality (e.g., polyp) rather than performing a physical biopsy. In another example, an identification of carcinoma can be used to avoid compromising a resection attempt.

According to another aspect of the present disclosure, in some implementations, the systems and methods of the present disclosure can provide for detection and mitigation of looping during a procedure. For example, by extracting the precise location and pose of the tip of the endoscopic device during a gastroenterological procedure, the computing system can identify or predict potential looping of the scope shaft and enable adjustment of the device to avoid such looping. By providing for mitigating looping of the scope shaft, the systems and methods of the present disclosure can avoid extended procedure times, incomplete examinations, and/or damage to the anatomical structure under examination (e.g., perforation of the colon wall, etc.).

According to another aspect of the present disclosure, in some implementations, the systems and methods of the present disclosure can provide for improvements in performance review of gastroenterological procedure and/or the like. For example, the systems and methods can provide for review of the navigation of an endoscopic device during a procedure, such as to review local navigation relative to landmarks to review completeness and accuracy, to determine velocity of the device during a procedure (e.g., determining if moving too quickly, etc.), and/or the like. For example, in some implementations, the systems and methods can provide for generating reports of per-procedure performance and quality. As one example, a per-procedure performance and quality report can indicate whether a procedure was executed adequately (e.g., quality, coverage, patient discomfort level, etc.), what abnormalities were detected along with positions of such detections (e.g., illustrated on a model), image data associated with such detected abnormalities, annotations generated by the operator (e.g., physician) during the procedure, and/or the like. In some implementations, data can be obtained and/or generated that may be indicative of a patient pain and/or discomfort level. Such data can facilitate adjustments to the operation of the endoscopic device and/or the like during a gastroenterological procedure to reduce and/or avoid pain and/or discomfort levels for the patient, and additionally provide for improved patient safety during a gastroenterological procedure.

The systems and methods of the present disclosure provide a number of technical effects and benefits. As one example, the systems and methods described herein can provide for improvements in abnormality (e.g., polyp) detection rates and the reliability of re-detection by providing more precise localization and positioning of an endoscopic device during procedures through the generation of a three-dimensional model and associated camera within the model. By providing more precise localization, the systems and methods can provide for improvements in diagnosis accuracy, for example, to be used in further endoscopic procedures and/or surgery.

The systems and methods of the present disclosure can provide additional technical effects and benefits of improving the detection and mitigation of looping during a procedure through knowledge of the exact location and pose of the tip of the endoscope. The mitigation of looping can provide for reduction in procedure times, more complete examinations, and avoiding damage to local anatomical structure.

As another example technical effect and benefit, the systems and methods of the present disclosure can provide real-time navigation assistance for an operator of an endoscopic device, which enables the operator to perform the procedure in a reduced amount of time. Performing faster, more efficient procedures saves computing resources such as processor usage, memory usage, and/or the like and also reduces the overall cost of performing the procedure.

With reference now to the Figures, example embodiments of the present disclosure will be discussed in further detail.

Example Devices and Systems

FIG. 1 depicts a block diagram of an example computing system 100 that can facilitate video-based positioning and navigation during medical procedures, such as gastroenterological procedures, according to example embodiments of the present disclosure. FIG. 1 illustrates one example computing system 100 that can be used to implement the present disclosure. Other computing systems that include different components can be used in addition or alternatively to the system 100. The system 100 may comprise one or more computing devices, such as computing device 102 and one or more remote computing devices (e.g., server computing systems, etc.), such as remote computing device 130, that are communicatively coupled over one or more networks, such as network 180.

The computing device 102 can be any type of computing device, such as, for example, a personal computing device (e.g., laptop or desktop), a server computing device, or any other type of computing device. The computing device 102 includes one or more processors 104 and one or more memories 106. The one or more processors 104 can be any suitable processing device (e.g., a processor core, a microprocessor, an ASIC, a FPGA, a controller, a microcontroller, etc.) and can be one processor or a plurality of processors that are operatively connected. The memory 106 can include one or more non-transitory computer-readable storage mediums, such as RAM, ROM, EEPROM, EPROM, flash memory devices, magnetic disks, etc., and combinations thereof. The memory 106 can store data 108 and instructions 110 which are executed by the processor 104 to cause the computing device 102 to perform operations, including one or more of the operations disclosed herein.

According to aspects of the present disclosure, the computing device 102 can include one or more systems 112 for mapping, navigation, and detection during a gastroenterological procedure that can implement features of the present disclosure. For example, the computing device 102 can obtain data comprising a video data stream generated by an endoscopic device during a gastroenterological procedure for a patient, and the mapping, navigation, and detection system(s) 112 can generate a three-dimensional model of at least a portion of an anatomical structure (e.g., colon, small intestine, etc.) viewed by the endoscopic device based at least in part on the video data stream. The mapping, navigation, and detection system(s) 112 can provide for mapping the anatomical structure and for the navigation of the endoscopic device. Additionally, the mapping, navigation, and detection system(s) 112 can provide for detection of one or more abnormalities (e.g., adenoma, polyp, lesion, tumor, etc.) within the portion of an anatomical structure (e.g., colon, small intestine, stomach, other internal organ, etc.) viewed by the endoscopic device (e.g., through the use of machine-learned models that have been trained for generating abnormality detection and/or re-detection probabilities) and provide for accurate positioning of the detected abnormalities, for example in association with the three-dimensional model. In addition, the mapping, navigation, and detection system(s) 112 can provide for generating visual presentation(s) of the three-dimensional model with the accurate positioning of any detected abnormalities thereon and provide the visual presentation for use in diagnosis and/or treatment of the patient. Further, in some implementations, the mapping, navigation, and detection system(s) 112 can provide for generating reports of procedure performance and quality, for example, to indicate whether a procedure was executed adequately, to indicate what abnormalities were detected along with positions of such detections, and/or the like.

The mapping, navigation, and detection system(s) 112 can include computer logic utilized to provide desired functionality. The mapping, navigation, and detection system(s) 112 can be implemented in hardware, firmware, and/or software controlling a processor, such as processor 104. For example, in some implementations, the mapping, navigation, and detection system(s) 112 include program files stored on a storage device, loaded into a memory such as memory 106 and executed by one or more processors such as processor 104. In other implementations, the mapping, navigation, and detection system(s) 112 include one or more sets of computer-executable instructions that are stored in a tangible computer-readable storage medium such as RAM hard disk or optical or magnetic media.

The computing device 102 can also include one or more input/output interface(s) 114. One or more input/output interface(s) 114 can include, for example, devices for receiving information from or providing information to a user, such as through a display device, touch screen, touch pad, mouse, data entry keys, an audio output device such as one or more speakers, a microphone, haptic feedback device, etc. The computing device 102 can also include one or more communication/network interface(s) 116 used to communicate with one or more systems or devices, including systems or devices that are remotely located from the computing device 102.

In some implementations, the computing device 102 can store or include one or more machine-learned models, such as a detection machine-learned model as discussed herein, for example, in association with or included within the mapping, navigation, and detection system(s) 112. For example, the machine-learned models can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks. Additional machine-learned models include support vector machines, decision-tree based models (e.g., random forests), regression models, and/or other types of models.

The remote computing device 140 can include one or more processors 142 and one or more memories 144. The one or more processors 142 can be any suitable processing device (e.g., a processor core, a microprocessor, an ASIC, a FPGA, a controller, a microcontroller, etc.) and can be one processor or a plurality of processors that are operatively connected. The memory 144 can include one or more non-transitory computer-readable storage mediums, such as RAM, ROM, EEPROM, EPROM, flash memory devices, magnetic disks, etc., and combinations thereof. The memory 144 can store data 146 and instructions 148 which are executed by the processor 142 to cause the remote computing device 140 to perform operations, for example, such as to implement operations as discussed herein. The remote computing device 140 may generate, store, process, and/or the like video data, procedure data, result data, medical device data, models, and/or the like which can be associated with implementation of one or more operations of the present disclosure, for example, by providing such data to the computing device 102. Any and all data can be stored, transmitted, or otherwise handled according to appropriate procedures to ensure patient confidentiality.

In some implementations, the remote computing system 140 includes or is otherwise implemented by one or more server computing devices. In instances in which the remote computing system 140 includes plural server computing devices, such server computing devices can operate according to sequential computing architectures, parallel computing architectures, or some combination thereof.

The remote computing device 140 can also include one or more communication/network interface(s) 150 used to communicate with one or more systems or devices, including systems or devices that are remotely located from the remote computing device 140, such as computing device 102, for example. The remote computing device 140 can also include one or more input/output interface(s) 152, for example, devices for receiving information from or providing information to a user.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

Figure 2:
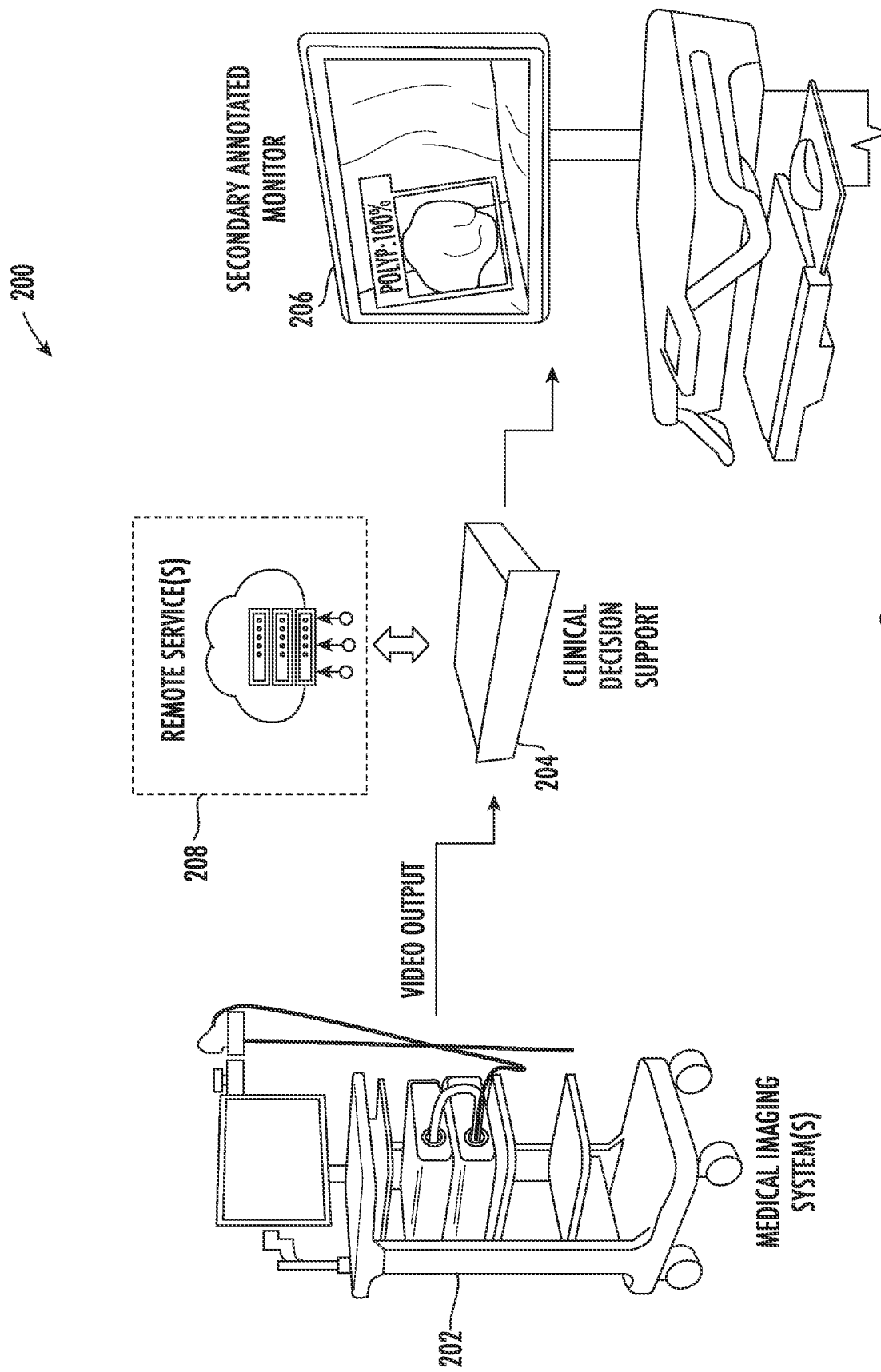
FIG. 2 depicts an example of a system for video-based positioning and navigation according to example embodiments of the present disclosure.

FIG. 2 depicts an example of a system 200 for video-based positioning and navigation in gastroenterological procedures according to example embodiments of the present disclosure. In some implementations, the system 200 for video-based positioning and navigation in gastroenterological procedures can provide for improvements in detection of abnormalities (e.g., polyps, lesions, tumors, etc.) as well as determining more precise locations of such abnormalities based on video signal data from an endoscopic device during a gastroenterological procedure. As illustrated in FIG. 2, in some implementations, the system 200 can include one or more medical imaging systems 202 (e.g., endoscopy systems, colonoscopy systems, etc.), a clinical support system 204, and a secondary presentation system 206. Additionally, in some implementations, the system 200 can include one or more remote services 208 (e.g., remote server computing systems, cloud-based services, etc.) that can communicate with the clinical support system 204 to facilitate performance of one or more operations such as disclosed herein.

The medical imaging system(s) 202 (e.g., endoscopic device, etc.) can be operated to provide for examination of an anatomical structure (e.g., colon, small intestine, stomach, other internal organ or body cavity, etc.) of a patient during a gastroenterological procedure. The medical imaging system(s) 202 can provide a video data stream output, for example, captured by a camera (e.g., endoscope, WCE, etc.) associated with the medical imaging system, as it is guided along a path within the anatomical structure. The medical imaging system(s) 202 can provide the video data stream as input to the clinical support system 204 for use in detection of abnormalities as part of the gastroenterological procedure.

The clinical support system 204 can perform real time processing of the video data stream input to provide for positioning and navigation of a camera of the medical imaging system 202 (e.g., endoscope, WCE, etc.) during the gastroenterological procedure. For example, according to aspects of the present disclosure, real time processing of the video data stream input (e.g., from an endoscope, WCE, etc.) can enable more precise localization, positioning, and navigation of an endoscopic device during a patient gastroenterological procedure, thereby improving detection rates and providing for the generation of visual presentations of procedure data, such as presentations of the anatomical structure (e.g., colon, small intestine, stomach, other internal organ, etc.), along with positions of any detected abnormalities (e.g., polyps, lesions, tumors, etc.).

The clinical support system 204 can provide for generation of a three-dimensional model of the anatomical structure (e.g., colon, small intestine, stomach, other internal organ, etc.) being examined and determination of the position of the camera (e.g., endoscope, WCE, etc.) in the anatomical structure at all times during the gastroenterological procedure. For example, in some implementations, a clinical support system 204 can perform simultaneous localization and mapping (SLAM) using the video data stream obtained from the medical imaging system 202 during the gastroenterological procedure. Using SLAM, the clinical support system 204 can generate and/or update a three-dimensional model of portions of the anatomical structure (e.g., colon, small intestine, stomach, other internal organ, etc.) of the patient viewed by the camera of the medical imaging system 202 (e.g., endoscope, etc.) as well as determine position/orientation data associated with any abnormalities (e.g., polyps, lesions, tumors, etc.) detected during the gastroenterological procedure.

The clinical support system 204 can provide for detection of abnormalities (e.g., polyps, lesions, tumors, etc.) during the gastroenterological procedure, for example, through the use of machine-learned models that have been trained to generate abnormality detection and/or re-detection probabilities during a gastroenterological procedure.

The clinical support system 204 can provide for generating output including visual representations, for example, based on the three-dimensional model, that can provide indications of the position(s) and/or orientation(s) of detected abnormalities (e.g., in association with the three-dimensional model, etc.), captured image data of the detected abnormalities, and/or the like, for example, for display via the secondary presentation system 206. In some implementations, the visual presentation output can further include operator (e.g., physician) generated notes made during the examination associated with each detected abnormality. The visual presentation can facilitate the diagnosis and/or treatment of the patient, performance review, and/or the like (e.g., optical biopsy, surgical determination, future endoscopic procedure, etc.). In some implementations, the visual presentation of the anatomical structure model, current position/viewpoint of the camera associated with the medical imaging system 202 (e.g., endoscope, etc.) and/or detected abnormality can be displayed by the secondary presentation system 206 in real-time, for example, to provide a heads-up display to the operator (e.g., physician, etc.) and combining different modalities of information in the visual presentation.

Additionally, in some implementations, the clinical support system 204 can provide for generation of a visibility map associated with the anatomical structure (e.g., colon, small intestine, stomach, other internal organ, etc.) being examined. By reconstructing the local three-dimensional structure, a visibility map can be generated and presented to the operator (e.g., physician, etc.), for example, via the secondary presentation system 206. The visibility map can provide a visual overlay of unviewed areas and/or suboptimally exposed areas based on the local three-dimensional structure, thus drawing operator attention (e.g., in real-time) to areas in need of further examination, thereby potentially improving the detection rate of the overall procedure.

In some implementations, the clinical support system 204 can provide for detection and mitigation of device looping during the gastroenterological procedure. For example, by extracting the precise location and pose of the tip of the camera associated with the medical imaging system 202 (e.g., endoscope, etc.) during the gastroenterological procedure can allow for identification of potential looping of the scope shaft and adjustments in guiding the scope to avoid such looping. By providing for mitigating looping of the scope shaft, the clinical support system 204 can help to avoid extended procedure times, incomplete examinations, and/or damage to the anatomical structure under examination (e.g., perforation of the colon wall, etc.).

Additionally, in some implementations, the clinical support system 204 can facilitate performance review and/or the like of a gastroenterological procedure. For example, the clinical support system 204 can generate output data to provide for review of the navigation of the camera associated with the medical imaging system 202 (e.g., endoscope, etc.) during the gastroenterological procedure, such as to review local navigation relative to landmarks to review completeness and accuracy, to determine velocity of the camera during a procedure (e.g., determining if moving too quickly, etc.), and/or the like. For example, in some implementations, the clinical support system 204 can provide for generating reports of per-procedure performance and quality data. As one example, per-procedure performance and quality data reports can indicate whether a procedure was executed adequately (e.g., quality, coverage, patient discomfort level, etc.), what abnormalities were detected along with positions of such detections (e.g., illustrated on representation of an anatomical structure model), image data associated with any detected abnormalities, annotations generated by the operator (e.g., physician, etc.) during the procedure, and/or the like. Any and all data can be stored, transmitted, or otherwise handled according to appropriate procedures to ensure patient confidentiality.

Additionally, in some embodiments, the system 200 can include one or more remote services 208 (e.g., remote server computing systems, cloud-based services, etc.) that can communicate with the clinical support system 204 to facilitate performance of one or more operations, such as providing operations associated with SLAM and/or abnormality detection, providing machine-learned model(s) to facilitate detection of abnormalities, providing standard atlases for use in generating three-dimensional models, and/or the like.

Figure 3:
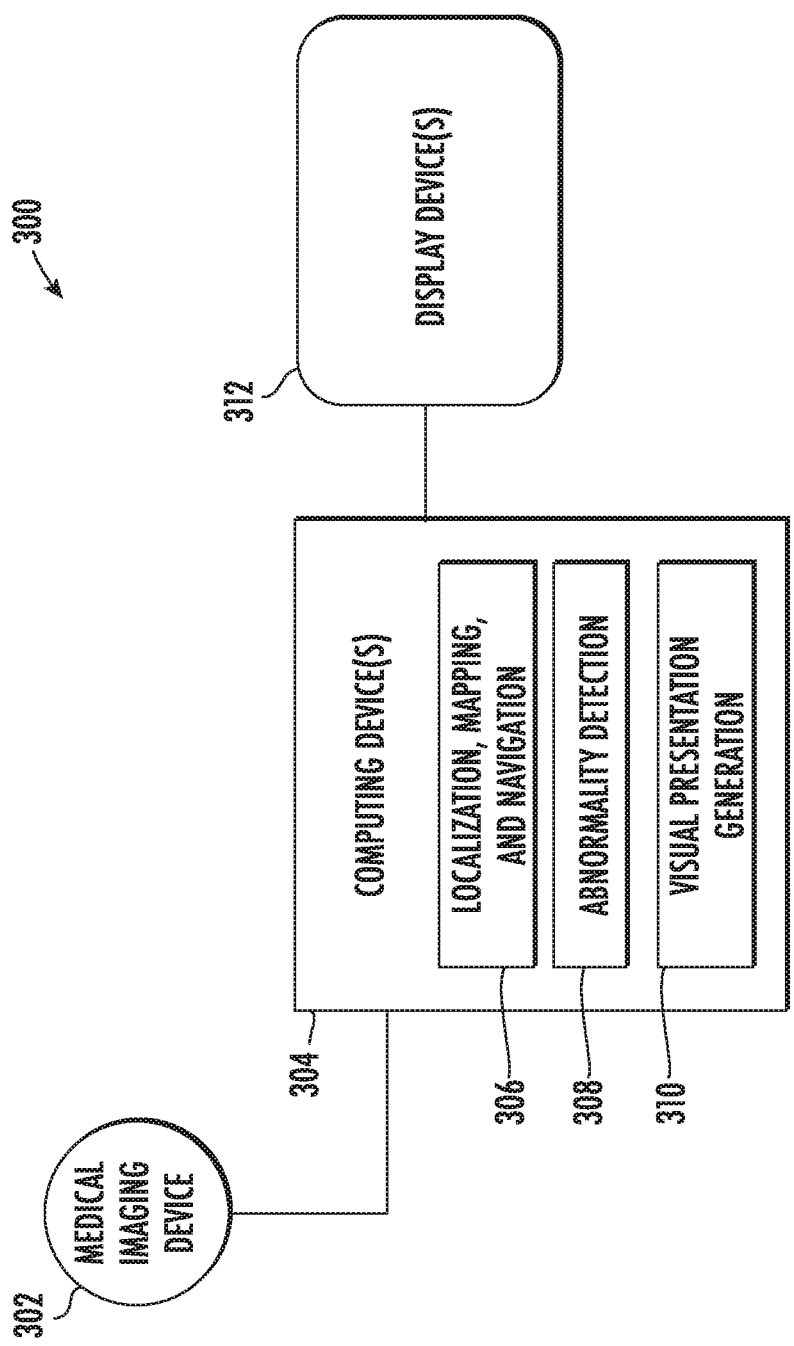
FIG. 3 depicts a block diagram of a system for video-based positioning and navigation according to example embodiments of the present disclosure.

FIG. 3 depicts a block diagram of a system 300 for video-based positioning and navigation in gastroenterological procedures according to example embodiments of the present disclosure. According to aspects of the present disclosure, the system 300 can facilitate improvements in the performance of gastroenterological procedures as well as improvements in the overall detection rate and reliability of detection of a gastroenterological procedure. For example, the system 300 for video-based positioning and navigation can enable more precise localization, positioning, and navigation of a medical imaging device (e.g., endoscope, WCE, etc.) as well as provide for improved detection of abnormalities (e.g., adenoma, polyp, lesion, tumor, etc.) and accuracy of position/orientation determinations of such abnormalities during a gastroenterological procedure.

In some implementations, as illustrated in FIG. 3, a system 300 for video-based positioning and navigation can include a medical imaging device 302 (e.g., an endoscopy system, colonoscopy system, etc.), one or more computing devices 304, and one or more presentation devices 312. The one or more computing devices 304 can include one or more systems to implement one or more of the operations as disclosed herein, which can include a localization-mapping-navigation system 306, an abnormality detection system 308, and a visual presentation generation system 310.

The medical imaging device 302 (e.g., endoscopic device, etc.) can be operated to provide for examination of an anatomical structure of a patient (e.g., colon, small intestine, stomach, other internal organ, etc.) during a gastroenterological procedure. The medical imaging device 302 can generate and provide a video data stream output as the device 302 is guided along a path within the anatomical structure of the patient. The medical imaging device 302 can provide the video data stream as input to the one or more computing devices 304, for example to facilitate more precise navigation of the medical imaging device 302 and provide for detection of one or more abnormalities as part of the gastroenterological procedure.

The computing device(s) 304 can perform processing of the video data stream input (e.g., in real-time) to provide for positioning and navigation of medical imaging device 302 (e.g., endoscope, etc.) during the gastroenterological procedure. For example, real time processing of the video data stream input can enable more precise localization, positioning, and navigation of medical imaging device 302 during the gastroenterological procedure, thereby facilitating improvements in performance of the gastroenterological procedure as well as abnormality detection rates and reliability.

The computing device(s) 304 can include a localization-mapping-navigation system 306 that provides for generation of a three-dimensional model of the anatomical structure (e.g., colon, small intestine, stomach, other internal organ, etc.) being examined and determination of the position of the medical imaging device 302 (e.g., endoscope, WCE, etc.) within the anatomical structure at all times during the gastroenterological procedure. For example, in some implementations, a localization-mapping-navigation system 306 can perform SLAM using the video data stream obtained from the medical imaging device 302 during the gastroenterological procedure. Using SLAM, the localization-mapping-navigation system 306 can generate and/or update a three-dimensional model of portions of the anatomical structure (e.g., colon, small intestine, stomach, other internal organ, etc.) of the patient viewed by the medical imaging device 302. Additionally, the localization-mapping-navigation system 306 can determine position/orientation data associated with any abnormalities (e.g., polyps, lesions, tumors, etc.) detected during the gastroenterological procedure.

The localization-mapping-navigation system 306 can include computer logic utilized to provide desired functionality. The localization-mapping-navigation system 306 can be implemented in hardware, firmware, and/or software controlling a general purpose processor. For example, in some implementations, the localization-mapping-navigation system 306 includes program files stored on a storage device, loaded into a memory and executed by one or more processors. In other implementations, the localization-mapping-navigation system 306 includes one or more sets of computer-executable instructions that are stored in a tangible computer-readable storage medium such as RAM hard disk or optical or magnetic media.

The computing device(s) 304 can also include an abnormality detection system 308 to facilitate detection of abnormalities (e.g., polyps, lesions, tumors, etc.) during the gastroenterological procedure. For example, the abnormality detection system 308 can provide for detection of abnormalities based on the use of one or more machine-learned models that have been trained to generate abnormality detection and/or re-detection probabilities during a gastroenterological procedure based on video image data input. For example, one or more machine-learned models can be trained to determine a probability of an abnormality (e.g., polyps, lesions, tumors, etc.) detection and/or re-detection based on a corpus of labeled image data (e.g., labeled image data comprising abnormalities detected in other examinations, etc.). In some implementations, the abnormality detection system 308 can provide for detection of abnormalities that may be on-screen for only one or two video frames (e.g., which may be difficult for a human operator to identify).

The abnormality detection system 308 can include computer logic utilized to provide desired functionality. The abnormality detection system 308 can be implemented in hardware, firmware, and/or software controlling a general purpose processor. For example, in some implementations, the abnormality detection system 308 includes program files stored on a storage device, loaded into a memory and executed by one or more processors. In other implementations, the abnormality detection system 308 includes one or more sets of computer-executable instructions that are stored in a tangible computer-readable storage medium such as RAI hard disk or optical or magnetic media.

The computing device(s) 304 can also include a visual presentation generation system 310 that can provide for generating output data based on the gastroenterological procedure. In some implementations, the visual presentation generation system 310 can generate visual presentations that provide indications of navigation and positioning of the medical imaging device 302, the current viewpoint of the medical imaging device 302, indications of any detected abnormalities (e.g., polyps, lesions, tumors, etc.), indications of the position(s) and/or orientation(s) of detected abnormalities, image data associated with the detected abnormalities, annotation data associated with a detected abnormality generated by the medical imaging device operator (e.g., physician, etc.), and/or the like. The computing device(s) 304 can provide for display of the output generated by the visual presentation generation system 310, for example, via presentation device(s) 312. The visual presentations generated by the visual presentation generation system 310 can facilitate the diagnosis and/or treatment of the patient (e.g., optical biopsy, surgical determination, future endoscopic procedure, etc.), performance review of the procedure, and/or the like. In some implementations, the output generated by the visual presentation generation system 310 can be displayed, for example via the presentation device(s) 312, in real-time to provide a heads-up type of display to the operator (e.g., physician, etc.) combining different modalities of information in the visual presentation. Any and all data can be stored, transmitted, or otherwise handled according to appropriate procedures to ensure patient confidentiality.

The visual presentation generation system 310 can include computer logic utilized to provide desired functionality. The visual presentation generation system 310 can be implemented in hardware, firmware, and/or software controlling a general purpose processor. For example, in some implementations, the visual presentation generation system 310 includes program files stored on a storage device, loaded into a memory and executed by one or more processors. In other implementations, the visual presentation generation system 310 includes one or more sets of computer-executable instructions that are stored in a tangible computer-readable storage medium such as RAM hard disk or optical or magnetic media.

Additionally, in some implementations, the localization-mapping-navigation system 306 and/or visual presentation generation system 310 can provide for generation of a visibility map associated with the anatomical structure (e.g., colon, small intestine, stomach, other internal organ) being examined. In some implementations, a visibility map can be generated, for example by reconstructing the local three-dimensional structure, and presented to the operator (e.g., physician, etc.) to provide indications of unviewed areas and/or sub-optimally exposed areas of the anatomical structure (e.g., colon, small intestine, stomach, other internal organ) being examined. The visibility map can draw the operator's attention (e.g., in real-time) to areas that may need further examination, thereby facilitating improvement in the overall abnormality detection rate of the gastroenterological procedure.

Further, in some implementations, the localization-mapping-navigation system 306 and/or visual presentation generation system 310 can provide for detection and mitigation of looping during a procedure. For example, by extracting the precise location and pose of the tip of the medical imaging device 302 during a gastroenterological procedure, the computing device(s) 304 can facilitate identification of potential looping of the device shaft and adjustment of the device navigation to avoid such looping.

Example Methods

Figure 4:
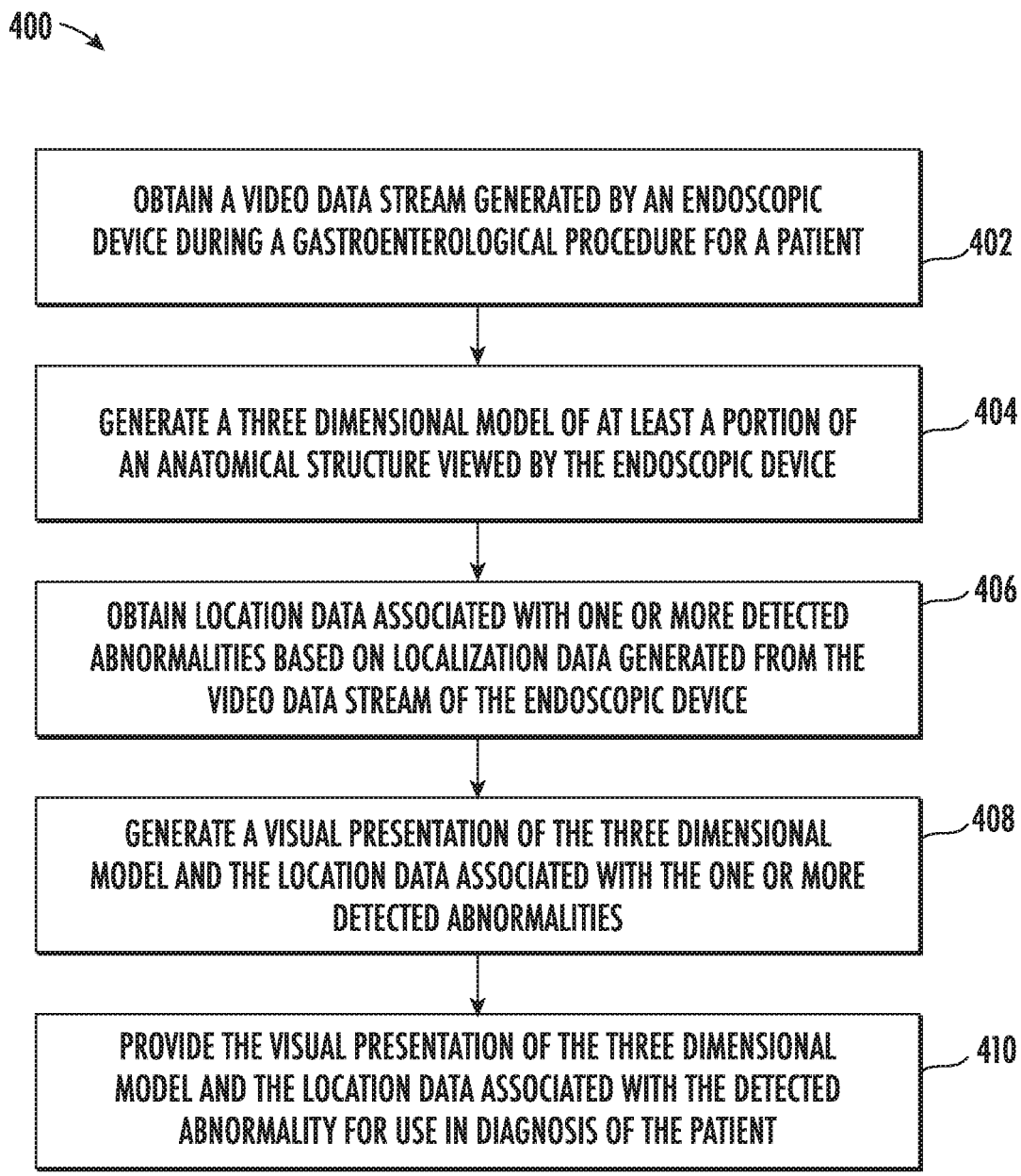
FIG. 4 depicts a flowchart diagram of an example method of video-based positioning and navigation for gastroenterological procedures according to example embodiments of the present disclosure.

FIG. 4 depicts a flowchart diagram of an example method 400 of video-based positioning and navigation for gastroenterological procedures according to example embodiments of the present disclosure. Although FIG. 4 depicts steps performed in a particular order for purposes of illustration and discussion, the methods of the present disclosure are not limited to the particularly illustrated order or arrangement. The various steps of the method 400 can be omitted, rearranged, combined, and/or adapted in various ways without deviating from the scope of the present disclosure. Method 400 can be implemented by one or more computing devices, such as one or more of the computing devices depicted in FIGS. 1-3.

At 402, method 400 can include a computing system obtaining a video data stream generated by a medical imaging system (e.g., endoscopic device, etc.) during a gastroenterological procedure for a patient. In particular, a medical imaging system (e.g., endoscopy system, etc.), such as illustrated in FIGS. 2 and 3, can be operated to provide for examination of an anatomical structure (e.g., colon, small intestine, stomach, other internal organ or body cavity, etc.) of a patient during a gastroenterological procedure. For example, the medical imaging system can generate a video data stream output, for example, as captured by a camera (e.g., endoscope, WCE, etc.) associated with the medical imaging system as it is navigated within the anatomical structure. The computing system can obtain the video data stream output from the medical imaging system that is generated as part of the gastroenterological procedure.

At 404, method 400 can include the computing system generating a three-dimensional model of at least a portion of the anatomical structure viewed by medical imaging system (e.g., endoscopic device, etc.) during the gastroenterological procedure. For instance, the computing system can generate a three-dimensional model of the anatomical structure (e.g., colon, small intestine, stomach, other internal organ, etc.) being examined and determine the position of the medical imaging system (e.g., endoscopic device, etc.) within the anatomical structure at all times during the gastroenterological procedure. For example, in some implementations, the computing system can perform simultaneous localization and mapping (SLAM) using the video data stream obtained from the medical imaging system during the gastroenterological procedure. In some implementations, using SLAM, the computing system can generate and/or update a three-dimensional model of portions of the anatomical structure (e.g., colon, small intestine, stomach, other internal organ, etc.) of the patient based on the image date stream provided from the medical imaging system.

Additionally, in some implementations, it is assumed that the anatomical structure under examination (e.g., colon, small intestine, stomach, other internal organ, etc.) is not a rigid structure, as it can undergo fluctuations during the procedure. In some implementations, the computing system can exploit the fact that an approximate structure of the anatomical structure (e.g., colon, small intestine, stomach, other internal organ, etc.) under examination is known, for example, by using standard atlases of colons in generating the three-dimensional model.

At 406, method 400 can include the computing system obtaining location and/or orientation data associated with one or more detected abnormalities, for example, based on localization data generated from the video data stream of the medical imaging system (e.g., endoscopic device, etc.). For example, the computing system can provide for detecting abnormalities (e.g., polyps, lesions, tumors, etc.) and/or obtain data regarding detected abnormalities during the gastroenterological procedure. The computing system can obtain position/orientation data associated with any abnormalities (e.g., polyps, lesions, tumors, etc.) detected during the gastroenterological procedure.

For example, the computing system can provide for detection of abnormalities based on the use of one or more machine-learned models that have been trained to generate abnormality detection and/or re-detection probabilities during a gastroenterological procedure based on video image data input. As an example, one or more machine-learned models can be trained to determine a probability of an abnormality (e.g., polyps, lesions, tumors, etc.) detection and/or re-detection based on a corpus of labeled image data (e.g., labeled image data comprising abnormalities detected in other examinations, etc.). In some implementations, the computing system can provide for detection of abnormalities that may be on-screen during the gastroenterological procedure for only one or two video frames (e.g., which may be difficult for a human operator to identify).

In some implementations, the computing system can perform global SLAM to determine the position of the abnormalities (e.g., polyps, lesions, tumors, etc.) and the pose of the medical imaging device (e.g., endoscope, etc.) as accurately as possible. In some implementations, the computing system can perform local SLAM to recover the local three-dimensional shape accurately in order to merge detections and estimate the orientation of the abnormality as accurately as possible, for example, to help determine the prior probability that the detector detects the abnormality. In some implementations, this data can be used to combine the detection results into a robust accurate detection probability.

Additionally, in some implementations, landmark detection can further allow for improved positioning, navigation, and detection during the gastroenterological procedure. For example, in some cases, such as in the little and large intestines, the position where the intestine twists can be quite easily detected and therefore the position of the abnormality can be defined as the part of the intestine between the twists and the distance from the last twist.

At 408, method 400 can include the computing system generating one or more visual presentations based on the three-dimensional model and the location data associated with the one or more detected abnormalities. For instance, in some implementations, the computing system can generate visual presentations that provide indications of navigation and positioning of the medical imaging device (e.g., endoscope, etc.), the current viewpoint of the medical imaging device (e.g., endoscope, etc.), indications of detected abnormalities (e.g., polyps, lesions, tumors, etc.), indications of the position(s) and/or orientation(s) of detected abnormalities, image data associated with the detected abnormalities, annotation data associated with a detected abnormality generated by the medical imaging device operator (e.g., physician, etc.), and/or the like.

At 410, method 400 can include the computing system providing the visual presentation based on the three-dimensional model and the location data associated with the detected abnormality for use in diagnosis of the patient. For example, the computing system can provide for display of the generated visual presentation output via one or more display devices, such as illustrated in FIGS. 2 and 3. In some implementations, the visual presentation(s) can facilitate the diagnosis and/or treatment of the patient (e.g., optical biopsy, surgical determination, future endoscopic procedure, etc.), performance reviews of the gastroenterological procedure, and/or the like. In some implementations, the visual presentation output generated by the computing system can be displayed, for example via the display device(s), in real-time to provide a heads-up type display to the operator of the medical imaging device (e.g., physician, etc.) combining different modalities of information in the visual presentation display.

Example Structures and Detections

Figure 5:
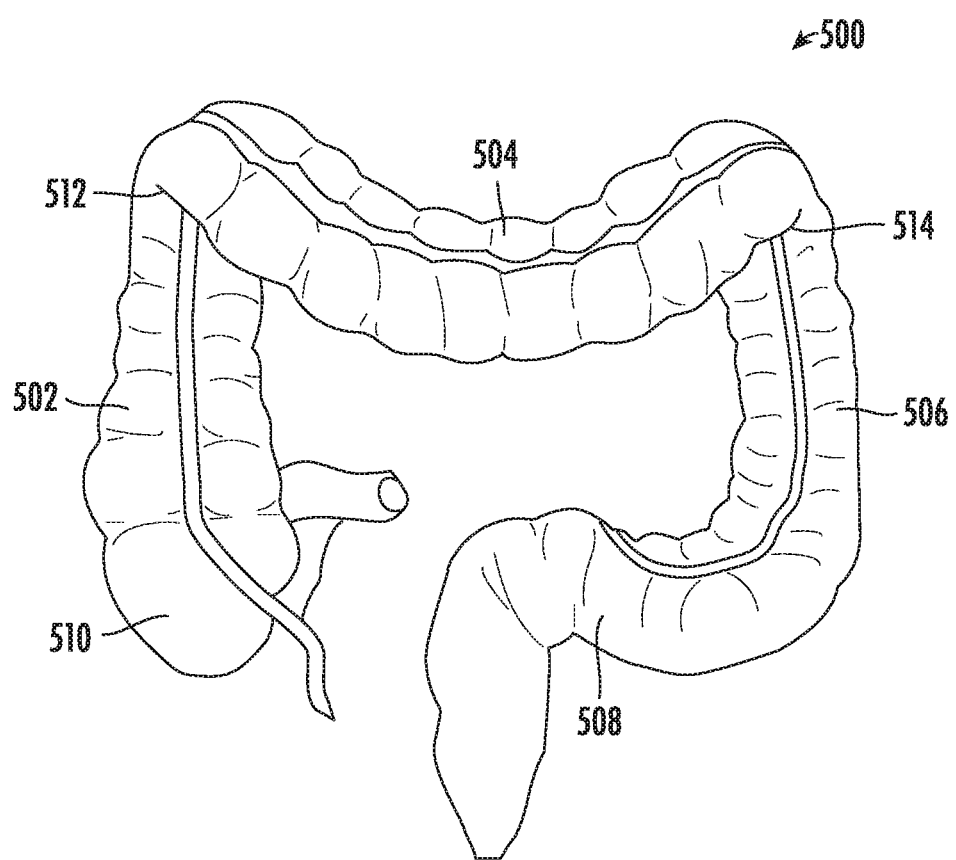
FIG. 5 depicts an example of an anatomical structure in which video-based positioning and navigation for gastroenterological procedures may be used according to example embodiments of the present disclosure.

FIG. 5 depicts an example illustration of a model colon 500 in which video-based positioning and navigation for a gastroenterological examination procedure may be performed according to example embodiments of the present disclosure. As discussed herein, the fact that an approximate structure of the anatomical structure (e.g., colon, etc.) under examination is known, for example, by using standard atlases of such anatomical structures in generating a three-dimensional model during a gastroenterological procedure. Further, in some implementations, landmark detection can further allow for improved positioning, navigation, and detection during a gastroenterological procedure.

A human colon, such as model colon 500, includes known structural components that can facilitate the generation of a three-dimensional model of a colon being examined during a gastroenterological procedure and/or identifying landmarks to provide improved positioning, navigation, and detection during a gastroenterological procedure. For example, as illustrated in FIG. 5, model colon 500 comprises the ascending colon 502, the transverse colon 504, the descending colon 506, and the sigmoid colon 508. In addition, a colon includes landmarks, such as the position where the colon twists, such as right hepatic flexure 512 and left splenic flexure 514, that can be easily detected and allow for defining a detected abnormality in relation the landmarks (e.g., defined as the part of the colon between the twists and the distance from the last twist, etc.). Additionally, in some implementations, the detection of important landmarks within an anatomical structure can provide for determination of examination adequacy (e.g., appropriate inspection velocity etc.) as well as provide for later performance review of the gastroenterological procedure.

Figure 6:
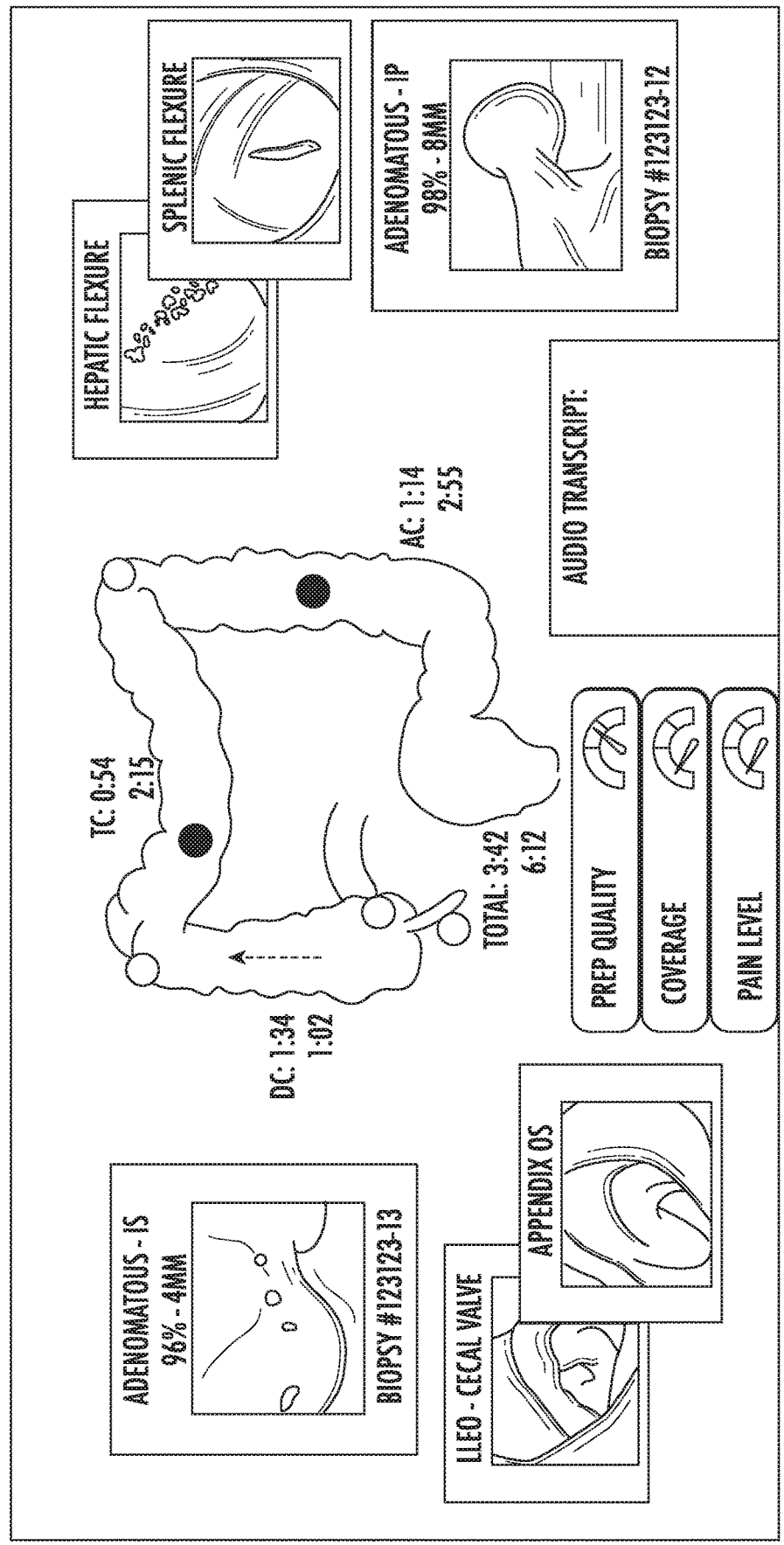
FIG. 6 depicts an example report output associated with video-based positioning and navigation for gastroenterological procedures according to example embodiments of the present disclosure.

FIG. 6 depicts an example report output 600 provided based on performance of video-based positioning and navigation for a gastroenterological procedure according to example embodiments of the present disclosure. As discussed herein, a computing system (e.g., as illustrated in FIGS. 1-3, etc.) can generate performance and quality reporting data, such as performance report 600, based on data generated during performance of video-based positioning and navigation during a gastroenterological procedure. For example, as illustrated in FIG. 6, a computing system can generate reporting data to provide for diagnosis based on a gastroenterological procedure, provide for performance review of a gastroenterological procedure, and/or the like. For instance, performance report 600 illustrates an example procedure performance and quality data output associated with a gastroenterological procedure. As an example, in some implementations, a per-procedure performance and quality report, such as report 600, can indicate whether a procedure was executed adequately (e.g., based on preparation quality measures, procedure coverage measures, patient discomfort/pain level measures, etc.), what abnormalities (e.g., polyps, lesions, tumors, etc.) were detected along with positions of such detections (e.g., illustrated on a representation of the anatomical structure), image data associated with detected abnormalities, annotations generated by the device operator (e.g., physician) during the procedure, and/or the like.

Figure 7:
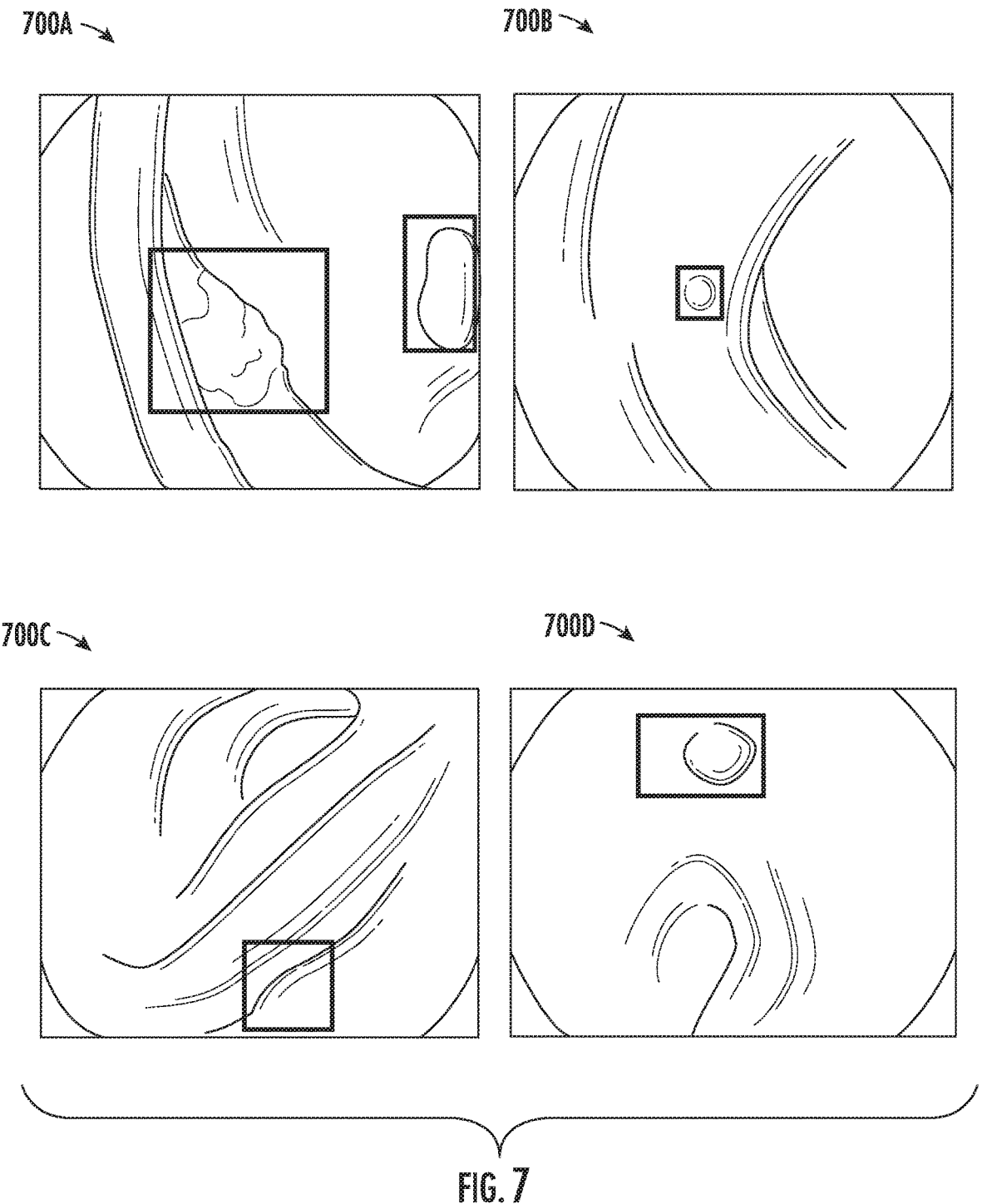
FIG. 7 depicts example detections associated with the performance of video-based positioning and navigation for gastroenterological procedures according to example embodiments of the present disclosure.

FIG. 7 depicts example images 700A-700D of detections associated with the performance of video-based positioning and navigation during gastroenterological procedures according to example embodiments of the present disclosure. As discussed, the systems and methods of the present disclosure can provide for improvements in detecting abnormalities (e.g., polyps, lesions, tumors, etc.) and determining more precise locations of abnormalities (e.g., polyps, lesions, tumors, etc.) based on video signal data from an endoscopic device (e.g., standard endoscope, WCE, etc.) during a gastroenterological procedures. For example, according to aspects of the present disclosure, real time processing of a video data stream (e.g., generated by an endoscopic device, etc.) can enable more precise localization, positioning, and navigation of an endoscopic device during a patient procedure, thereby improving polyp detection rates and providing for the generation of visual presentations of procedure data (e.g., detection of abnormalities, position/orientation of abnormalities, etc.). As illustrated in FIG. 7, the systems and methods of the present disclosure can provide for the detection of abnormalities (e.g., polyps, lesions, tumors, etc.) during a gastroenterological procedure.

As one example, image 700A illustrates an example detection of a carcinoma to the lower left of the image 700A and a polyp to the right side of image 700A. As another example, image 700B illustrates an example detection of a small adenomatous polyp near the center of image 700B. In another example, image 700C illustrates an example detection of a hyperplastic polyp at the bottom center of image 700C. As another example, image 700D illustrates an example detection of a polyp at the top center of image 700C that was detected even though it was only visible in one or two frames of the video captured during the procedure.

Figure 8:
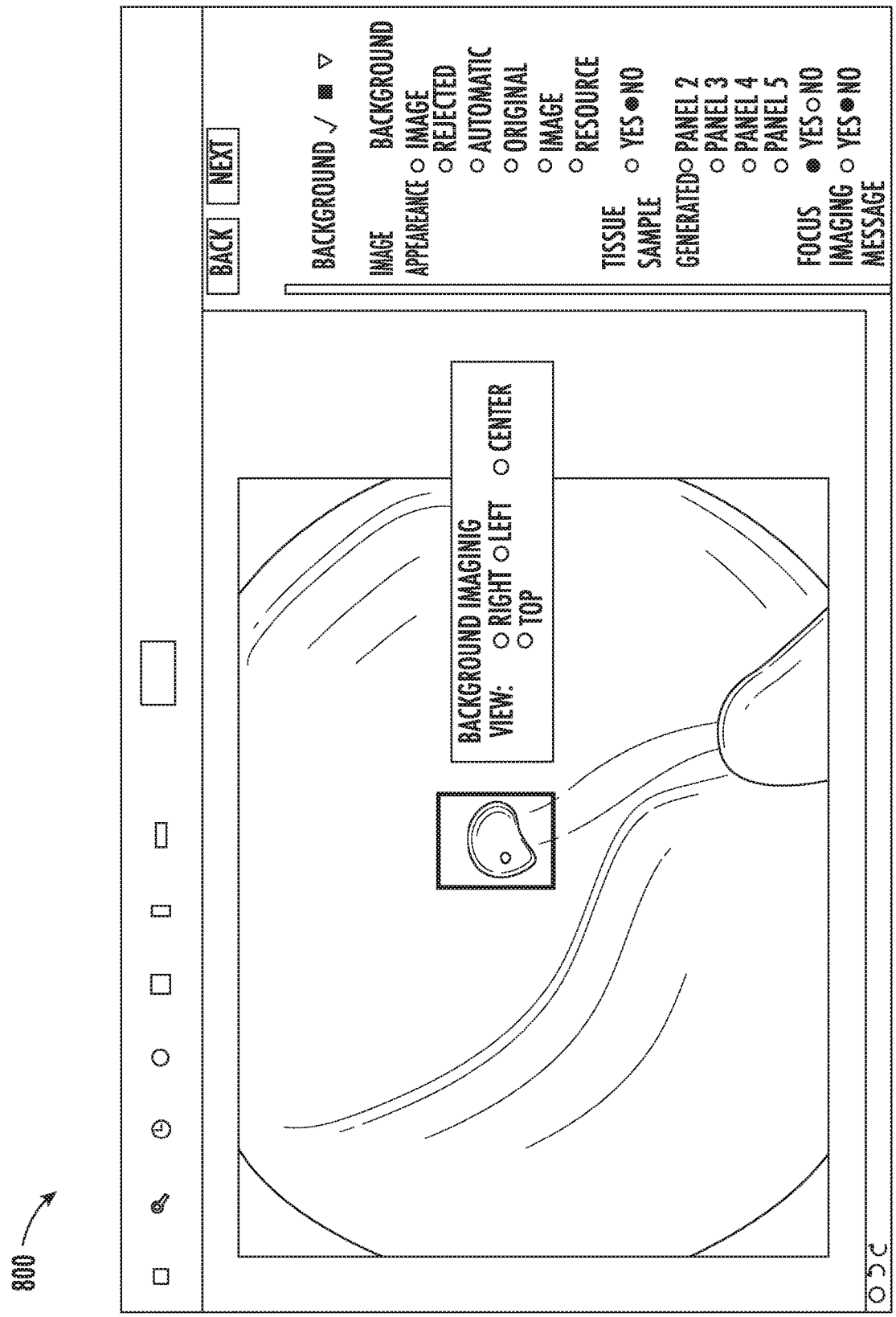
FIG. 8 depicts example output interface associated with the performance of video-based positioning and navigation for gastroenterological procedures according to example embodiments of the present disclosure.

FIG. 8 depicts an example detection output interface 800 associated with the performance of video-based positioning and navigation during a gastroenterological procedure according to example embodiments of the present disclosure. As illustrated in FIG. 8, interface 800 provides an indication of an abnormality detected during a gastroenterological procedure.

Additional Disclosure

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:
1. A computer-implemented method, the method comprising:
receiving, by one or more computing devices, a video data stream generated by an endoscopic device during a gastroenterological procedure for a patient;

generating, by the one or more computing devices, a three-dimensional model of at least a portion of an anatomical structure viewed by the endoscopic device;

updating, by the one or more computing devices, the three-dimensional model based on simultaneous localization and mapping performed on local regions of the anatomical structure based at least in part on the video data stream;

obtaining, by the one or more computing devices, location data associated with one or more detected abnormalities based on the three-dimensional model updated based on the simultaneous localization and mapping performed on the local regions of the anatomical structure;

generating, by the one or more computing devices, a visual presentation of the three-dimensional model updated based on the simultaneous location and mapping and the location data associated with the one or more detected abnormalities; and providing, by the one or more computing devices, the visual presentation of the three-dimensional model updated based on the simultaneous localization and mapping and the location data associated with the one or more detected abnormalities for use in diagnosis of the patient.

2. The computer-implemented method of claim 1, wherein generating, by the one or more computing devices, the three-dimensional model is based on simultaneous localization and mapping performed using the video data stream.

3. The computer-implemented method of claim 1, wherein providing, by the one or more computing devices, the visual presentation of the three-dimensional model updated based on the simultaneous localization and mapping and the location data associated with the one or more detected abnormalities for use in diagnosis of the patient is performed in real-time during the gastroenterological procedure.

4. The computer-implemented method of claim 1, wherein the method further comprises obtaining, by the one or more computing devices, a probability of an abnormality detection based on a three-dimensional reconstruction of a local region of the anatomical structure.

5. The computer-implemented method of claim 4, wherein the three-dimensional reconstruction of the local region of the anatomical structure is used in determining a physical location of a detected polyp within the local region.

6. The computer-implemented method of claim 4, wherein the three-dimensional reconstruction of the local region of the anatomical structure is used in estimating an orientation of a detected polyp.

7. The computer-implemented method of claim 1, wherein the method further comprises generating, by the one or more computing devices, a visibility map based on the three-dimensional model and navigation data associated with the endoscopic device, the visibility map comprising a visual overlay indicative of unviewed areas of the anatomical structure.

8. The computer-implemented method of claim 1, wherein the visual presentation includes physician-generated note data associated with the one or more detected abnormalities generated during the gastroenterological procedure.

9. The computer-implemented method of claim 1, wherein generating, by the one or more computing devices, the three-dimensional model of at least the portion of the anatomical structure viewed by the endoscopic device comprises:

obtaining, by the one or more computing devices, one or more generic anatomical structures to be used as a base for the three-dimensional model and updating, by the one or more computing devices, the three-dimensional model from the generic anatomical structure based at least in part on the video data stream of the endoscopic device.

10. The computer-implemented method of claim 1, wherein the method further comprises:

determining, by the one or more computing devices, a probability of an abnormality detection using a trained machine-learned model that has been trained to identify abnormalities within a gastrointestinal tract from video data associated with the gastrointestinal tract.

11. The computer-implemented method of claim 1, wherein the method further comprises:

identifying, by the one or more computing devices, looping of an endoscopic device shaft during the gastroenterological procedure based on a localization and a pose of a tip of the endoscopic device.

12. One or more non-transitory computer-readable media that store instructions that, when executed by one or more processors of a computing system, cause the computing system to carry out actions comprising:

receiving, by one or more computing devices of the computing system, a video data stream generated by an endoscopic device during a gastroenterological procedure for a patient;

generating, by the one or more computing devices, a three-dimensional model of at least a portion of an anatomical structure viewed by the endoscopic device;

obtaining, by the one or more computing devices, location data associated with one or more detected abnormalities based on localization data generated from the video data stream of the endoscopic device;

generating, by the one or more computing devices, a visual presentation of the three-dimensional model and the location data associated with the one or more detected abnormalities;

providing, by the one or more computing devices, the visual presentation of the three-dimensional model and the location data associated with the detected abnormality for use in diagnosis of the patient; and obtaining, by the one or more computing devices, a probability of an abnormality detection based on a three-dimensional reconstruction of a local region of the anatomical structure;

wherein the three-dimensional reconstruction of the local region of the anatomical structure is used in determining a physical location of a detected polyp within the local region or is used in estimating an orientation of a detected polyp.

13. The computer-readable media of claim 12, wherein the actions further comprise:

updating, by the one or more computing devices, the three-dimensional model based on simultaneous localization and mapping performed on local regions of the anatomical structure based at least in part on the video data stream; and obtaining, by the one or more computing devices, location data associated with one or more detected abnormalities based on the three-dimensional model updated based on the simultaneous localization and mapping performed on the local regions of the anatomical structure.

14. The computer-readable media of claim 12, wherein generating, by the one or more computing devices, the three-dimensional model of at least the portion of the anatomical structure viewed by the endoscopic device comprises:
  obtaining, by the one or more computing devices, one or more generic anatomical structures to be used as a base for the three-dimensional model and
  updating, by the one or more computing devices, the three-dimensional model from the generic anatomical structure based at least in part on the video data stream of the endoscopic device.

15. The computer-readable media of claim 12, wherein the actions further comprise:
  determining, by the one or more computing devices, a probability of an abnormality detection using a trained machine-learned model that has been trained to identify abnormalities within a gastrointestinal tract from video data associated with the gastrointestinal tract.

16. The computer-readable media of claim 12, wherein the actions further comprise:
  identifying, by the one or more computing devices, looping of an endoscopic device shaft during the gastroenterological procedure based on a localization and a pose of a tip of the endoscopic device.

17. One or more non-transitory computer-readable media that store instructions that, when executed by one or more processors of a computing system, cause the computing system to carry out actions comprising:
  receiving, by one or more computing devices of the computing system, a video data stream generated by an endoscopic device during a gastroenterological procedure for a patient;
  generating, by the one or more computing devices, a three-dimensional model of at least a portion of an anatomical structure viewed by the endoscopic device;
  obtaining, by the one or more computing devices, location data associated with one or more detected abnormalities based on localization data generated from the video data stream of the endoscopic device;
  generating, by the one or more computing devices, a visual presentation of the three-dimensional model and the location data associated with the one or more detected abnormalities; and
  providing, by the one or more computing devices, the visual presentation of the three-dimensional model and the location data associated with the detected abnormality for use in diagnosis of the patient;
  wherein generating, by the one or more computing devices, the three-dimensional model of at least the portion of the anatomical structure viewed by the endoscopic device comprises:
    obtaining, by the one or more computing devices, one or more generic anatomical structures to be used as a base for the three-dimensional model and
    updating, by the one or more computing devices, the three-dimensional model from the generic anatomical structure based at least in part on the video data stream of the endoscopic device.

* * * * *